(12) United States Patent
Wang

(10) Patent No.: US 8,489,166 B2
(45) Date of Patent: Jul. 16, 2013

(54) SOFT GUM FINGERSTALL OXIMETER WITHOUT PIVOT STRUCTURE

(75) Inventor: Weihu Wang, Beijing (CN)

(73) Assignee: Beijing Choice Electronic Technology Co., Ltd., Beijing (CN)

( * ) Notice: Subject to any disclaimer, the term of this patent is extended or adjusted under 35 U.S.C. 154(b) by 631 days.

(21) Appl. No.: 12/670,281

(22) PCT Filed: Mar. 21, 2008

(86) PCT No.: PCT/CN2008/070412
§ 371 (c)(1),
(2), (4) Date: Jan. 22, 2010

(87) PCT Pub. No.: WO2009/114963
PCT Pub. Date: Sep. 24, 2009

(65) Prior Publication Data
US 2010/0198028 A1 Aug. 5, 2010

(51) Int. Cl.
*A61B 5/00* (2006.01)

(52) U.S. Cl.
USPC .......................................................... 600/323

(58) Field of Classification Search
USPC ................................ 600/322, 323, 340, 344
See application file for complete search history.

(56) References Cited

U.S. PATENT DOCUMENTS

| 5,337,744 | A | 8/1994 | Branigan | |
|---|---|---|---|---|
| 5,452,717 | A | 9/1995 | Branigan et al. | |
| 5,776,059 | A | 7/1998 | Kaestle et al. | |
| 6,571,114 | B1 * | 5/2003 | Koike et al. | 600/323 |
| 6,654,621 | B2 * | 11/2003 | Palatnik et al. | 600/322 |
| 7,104,673 | B2 * | 9/2006 | Yu | 362/396 |
| 7,657,294 | B2 * | 2/2010 | Eghbal et al. | 600/344 |
| 2007/0071643 | A1 * | 3/2007 | Hall et al. | 422/62 |

FOREIGN PATENT DOCUMENTS

| CN | 2177449 Y | 9/1994 |
|---|---|---|
| CN | 1141585 A | 1/1997 |
| JP | 2007117641 A | 5/2007 |

* cited by examiner

*Primary Examiner* — Clayton E LaBalle
*Assistant Examiner* — Minh Phan
(74) *Attorney, Agent, or Firm* — The Webb Law Firm

(57) ABSTRACT

The present invention discloses a soft gum fingerstall oximeter without pivot structure, the soft gum fingerstall oximeter comprises a soft gum fingerstall which can wraps around a finger closely with variations of the profile of the finger and causes a clamping force distributed on the clamped portion of the finger uniformly. An emission circuit board and a reception circuit board are provided in the soft gum fingerstall. The soft gum fingerstall of the oximeter is enclosed, which can shield light entering from a side.

4 Claims, 3 Drawing Sheets

SOFT GUM FINGERSTALL OXIMETER WITHOUT PIVOT STRUCTURE

FIELD OF THE INVENTION

The present invention relates to a finger clip oximeter, and particularly relates to a soft gum fingerstall oximeter without pivot structure.

BACKGROUND OF THE INVENTION

Generally, a finger clip oximeter according to the prior art includes an upper case and a lower case which are connected with each other by a pivot, can be rotated around the pivot relatively and be separated by a certain distance from each other. The upper and lower cases apply a clamping pressure to a nail of a measured finger by a coil spring.

However, when the finger clip oximeter clamps the nail to perform oximetric measurement, the upper and lower cases are opened a certain angle with respect to each other necessarily. After the upper and lower cases are opened, light will enter from a side thereby to influence the measurement result in case that the light is strong. Different persons have different sizes of fingers, therefore, the angles which the upper and lower cases are opened with respect to each other are different and the influences owing to light entering from a side are different as well. Accordingly, the finger clip oximeter is hard to perform calibration on fingers with various sizes in advance, so that a light path offset occurs easily during its practical use resulting in a measuring error.

In addition, in the finger clip oximeter according to the prior art, a finger clamping portion of the upper and lower cases applies a non uniform force to a finger along the length of the finger, and the smaller clamping force exists in the location which is more away from the hinged pivot. Because different users are different largely in sizes of fingers, the clamping portion of the finger clip oximeter according to the prior art can only be defined within a prescribed range of size, and it is impossible that any specific finger clip oximeter according to the prior art is applicable to a finger which is too thick or too thin. Therefore, the range in which the finger clip oximeter according to the prior art can be applied is limited. Further, for a user with thicker fingers, the user's fingers are not comfortable when he uses the finger clip oximeter according to the prior art.

Since the finger clip oximeter according to the prior art is limited in its structure, a portion where the cases contact with a finger can not be cleaned conveniently and thoroughly. Therefore, there is a risk of cross propagation of bacteria among different users in use.

Also, the finger clip oximeter according to the prior art is complicated in structure and difficult to be assembled.

SUMMARY OF THE INVENTION

An object of the present invention is to provide a soft gum fingerstall oximeter without pivot structure which can shield light entering from a side and can be used normally to obtain an accurate measurement result in a strong light environment.

Another object of the present invention is to provide a soft gum fingerstall oximeter without pivot structure which can reduce a light path offset and improve accuracy of measurement.

Still another object of the present invention is to provide a soft gum fingerstall oximeter without pivot structure, in which the soft gum fingerstall wraps around a finger closely with variations of the profile of the finger and a clamping force is distributed on the clamped portion of the finger uniformly by use of the physical flexibility of silicon rubber, so that a human-machine contact surface is changed and comfort is improved.

Yet still another object of the present invention is to provide a soft gum fingerstall oximeter without pivot structure, in which a portion where the cases contact with a finger can be cleaned conveniently and thoroughly, thus, there is no risk of cross propagation of bacteria among the users in use.

Again yet still another object of the present invention is to provide a soft gum fingerstall oximeter without pivot structure, in which the structure of the product is simplified and the reliability of the product is improved.

For this reason, the invention provides a soft gum fingerstall oximeter without pivot structure, characterized in that the soft gum fingerstall oximeter comprises a soft gum fingerstall which wraps around a finger with variations of the profile of the finger and causes a clamping force distributed on the clamped portion of the finger uniformly, and an emission circuit board and a reception circuit board are provided in the soft gum fingerstall.

Preferably, the soft gum fingerstall oximeter further comprises a housing in which electronic elements including a data processing circuit board, a test report display screen, operation keys, a battery, a speaker and a mini USB data output port are provided, and the housing is provided on a side outside of the soft gum fingerstall and is connected to the soft gum fingerstall detachably.

Preferably, the soft gum fingerstall oximeter further comprising a circuit unit which includes a data processing circuit board, measuring circuit boards, a test report display screen, operation keys and a battery; and a soft silica gel sheath in which the circuit unit is provided and which has an opening through which fingers can be inserted into, and the measuring circuit boards include an emission circuit board and a reception circuit board which are provided opposite to each other.

Preferably, the emission circuit board is provided inside the soft silica gel sheath on a side in which a measured finger contacts with an inner surface of the soft silica gel sheath in a measurement, and the reception circuit board which is provided opposite to the emission circuit board is provided inside the soft silica gel sheath on a side in which the data processing circuit board is located.

Preferably, a stainless steel connecting plate which is used to fix and protect the electronic elements is imbedded in the soft silica gel sheath, the stainless steel connecting late is hot pressed to and inserted into the soft silica el sheath to form a single unit, and the outline of the stainless steel connecting plate varies with profiles of a top surface and side surfaces of the soft silica gel sheath.

Preferably, electronic elements including a data processing circuit board, a test report display screen, operation keys, a battery, a speaker and a mini USB data output port are provided in a housing in which horizontal dragging slideways for soft gum slide plates are provided, an upper soft gum fingerstall and a lower soft gum fingerstall are fixed to the soft gum slide plates respectively, while the soft gum slide plates are mounted on the horizontal dragging slideways for the soft gum slide plates in the housing respectively, measuring elements are attached to the soft gum fingerstalls, and the measuring elements attached to the soft gum fingerstalls are connected to an interface circuit board in the housing via a pin socket.

The soft gum fingerstall oximeter according to the present invention has an enclosed silica gel fingerstall which can shield light entering from a side so that the oximeter can be used normally to obtain an accurate measurement result in a strong light environment.

The soft gum fingerstall oximeter according to the present invention has an enclosed silica gel fingerstall which can reduce a light path offset and improve accuracy of measurement.

The soft gum fingerstall oximeter according to the present invention has an enclosed silica gel fingerstall in which the soft gum fingerstall wraps around a finger closely with variations of the profile of the finger by use of the physical flexibility of silicon rubber and causes a clamping force distributed on the clamped portion of the finger uniformly so that a human-machine contact surface is changed and comfort is improved.

The soft gum fingerstall oximeter according to the present invention has an enclosed silica gel fingerstall in which a portion where the cases contact with a finger can be cleaned conveniently and thoroughly by use of the physical flexibility of silicon rubber, thus, there is no risk of cross propagation of bacteria among the users in use.

The soft gum fingerstall oximeter according to the present invention has an enclosed silica gel fingerstall in which the structure of the product is simplified and the reliability of the product is improved by eliminating the pivot and the coil spring in the prior art.

DETAILED DESCRIPTION OF THE PREFERRED EMBODIMENTS

Figure 1A:
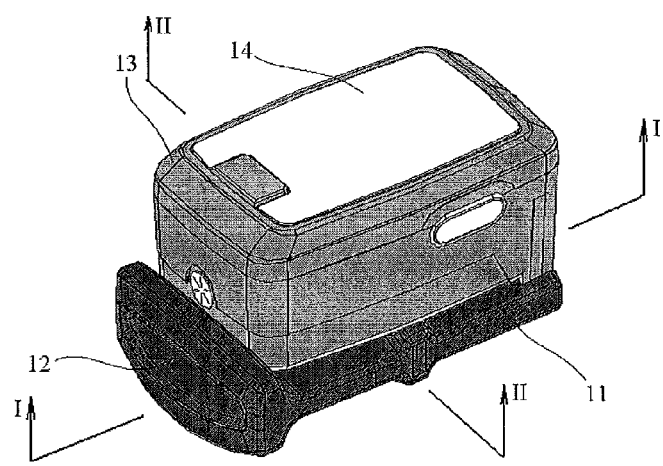
FIG. 1A is a perspective diagram of a soft gum fingerstall oximeter according to a first embodiment of the present invention.
Figure 1B:
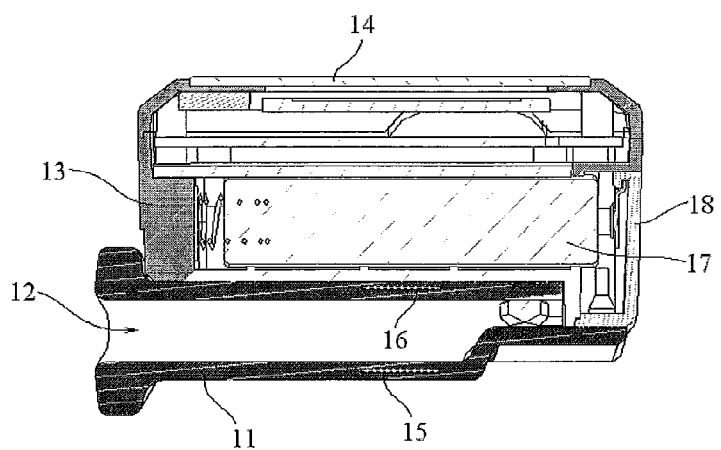
FIG. 1B is a longitudinal section view along a line I-I in FIG. 1A.
Figure 1C:
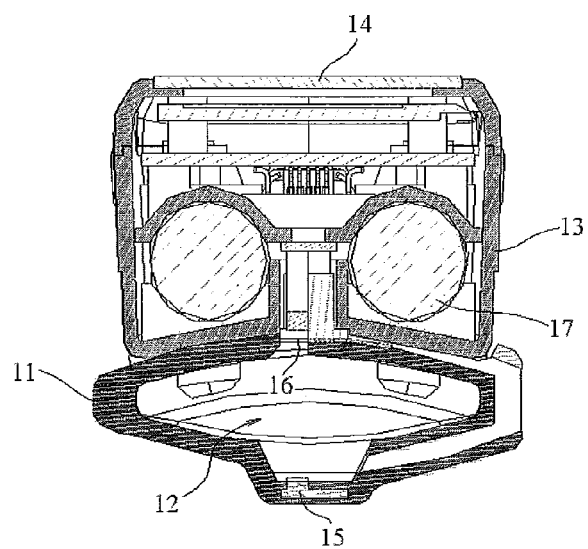
FIG. 1C is a transverse section view along a line II-II in FIG. 1A.

According to a first embodiment of the present invention, as shown in FIGS. 1A, 1B and 1C, a soft gum fingerstall oximeter is a box like oximeter which includes a housing 13 and a silica gel fingerstall 11. The housing 13 is provided outside the silica gel fingerstall 11 which is a soft fingerstall and on which a number of umbrella shaped connectors (not shown) are provided. These umbrella shaped connectors can be snapped into the housing 13 to connect the silica gel fingerstall 11 with the housing 13.

If the silica gel fingerstall 11 is required to be replaced, all we need is to hold the housing 13 and pull the silica gel fingerstall 11 with a little force, that is, the silica gel fingerstall 11 can be separated from the housing 13 conveniently.

In this embodiment, measuring elements 15, 16 are provided on the silica gel fingerstall 11. A data processing circuit board, a test report display screen 14, operation keys, a battery 17, a speaker, a mini USB data output port and the like are provided in the housing 13. The measuring elements 15, 16 fixed to the silica gel fingerstall 11 are connected to an interface circuit board in the housing 13 via a pin socket. A reference numeral 18 denotes a battery cap.

When a finger is inserted into the silica gel fingerstall 11 from an opening 12 of the silica gel fingerstall 11, the silica gel fingerstall 11 wraps around the finger closely with variations of the profile of the finger and causes a clamping force distributed on the clamped portion of the finger uniformly.

The silica gel fingerstall 11 has a wider elastic range, which is adaptable to a larger variation of the sizes of fingers.

The silica gel fingerstall 11 is in a totally enclosed form, which prevents the side strong light from disturbing the measurement.

Since a pivot structure is eliminated, the reliability of the oximeter is improved.

Figure 2A:
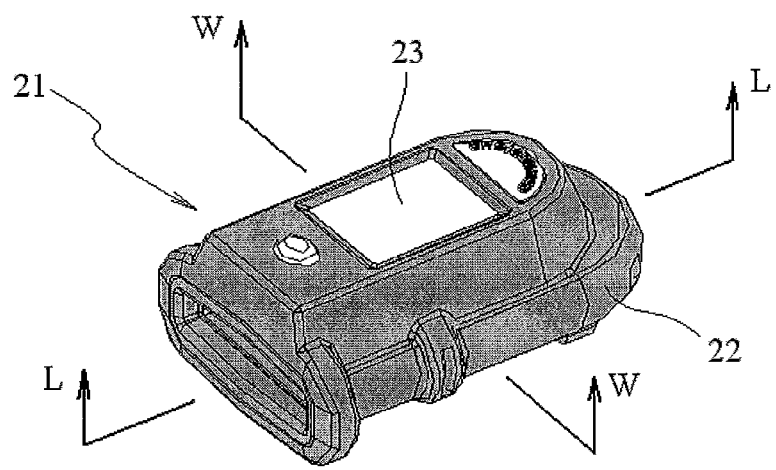
FIG. 2A is a perspective diagram of a soft gum fingerstall oximeter according to a second embodiment of the present invention.
Figure 2B:
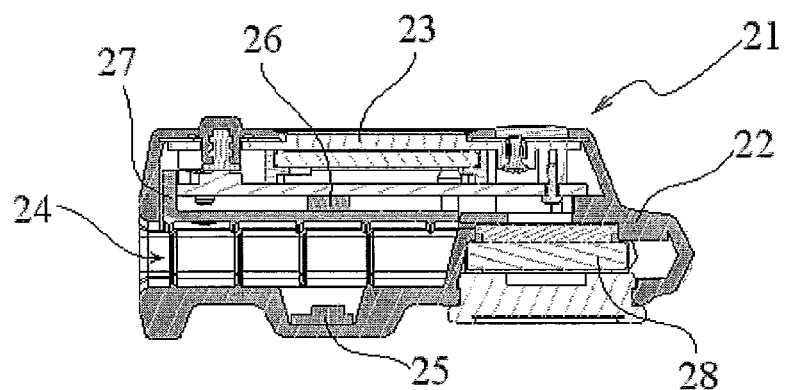
FIG. 2B is a longitudinal section view along a line L-L in FIG. 2A.
Figure 2C:
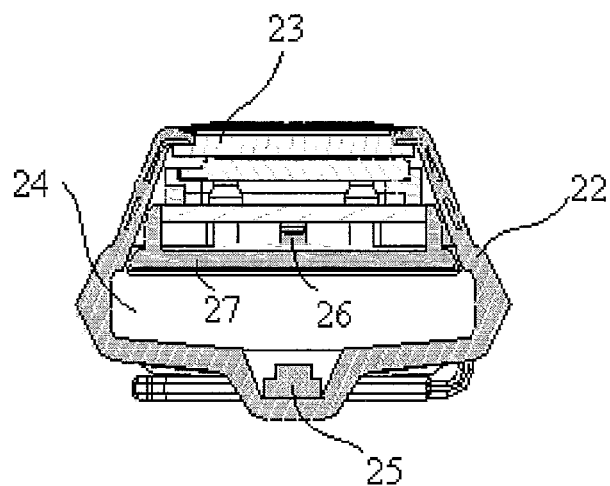
FIG. 2C is a transverse section view along a line W-W in FIG. 2A.

According to a second embodiment of the present invention, as shown in FIGS. 2A, 2B and 2C, a soft gum fingerstall oximeter 21 is an integral soft silica gel sheath oximeter in which all of electronic elements are placed in a soft silica gel sheath 22.

In order that all of the electronic elements are fixed within the soft silica gel sheath 22, a stainless steel connecting plate, which is hot pressed to and inserted into the soft silica gel sheath 22 to form a single unit, is imbedded in the soft silica gel sheath 22. The outline of the connecting plate varies along profiles of a top surface and side surfaces of the soft silica gel sheath 22 to function as fixing and protecting the elements.

A data processing circuit board 27, measuring circuit boards 25, 26, a test report display screen 23, operation keys, a battery 28, a speaker, a mini USB data output port and the like are provided in the soft silica gel sheath 22.

When a finger is inserted into the soft silica gel sheath 22 from an opening 24, soft silica gel sheath 22 wraps around the finger closely with variations of the profile of the finger and causes a clamping force distributed on the clamped portion of the finger uniformly.

The soft silica gel sheath 22 has a wider elastic range, which is adaptable to a larger variation of the sizes of fingers.

In this embodiment, because all of the electronic elements are contained in the soft silica gel sheath 22, the material of the sheath can absorb impact force from the exterior, thus the soft silica gel sheath further has a drop-proof function.

The soft silica gel sheath 22 is in a totally enclosed form, which prevents the side strong light from disturbing the measurement.

Since a pivot structure is eliminated, the reliability of the oximeter is improved.

Figure 3A:
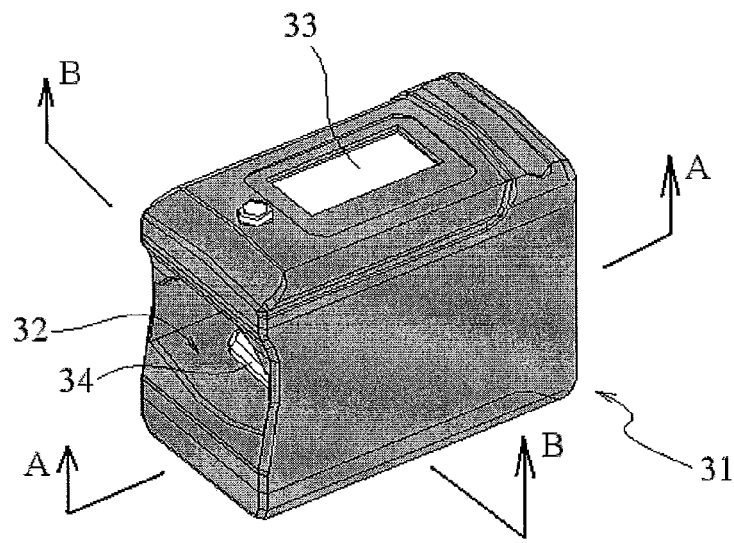
FIG. 3A is a perspective diagram of a soft gum fingerstall oximeter according to a third embodiment of the present invention.
Figure 3B:
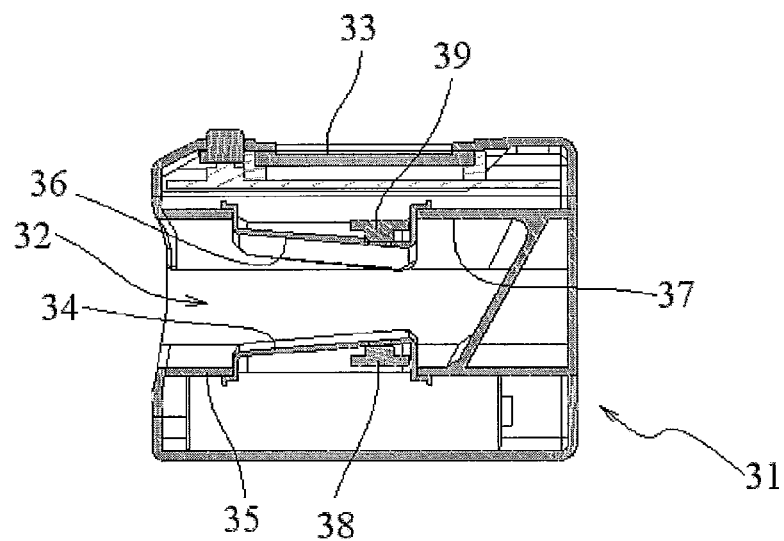
FIG. 3B is a longitudinal section view along a line A-A in FIG. 3A.
Figure 3C:
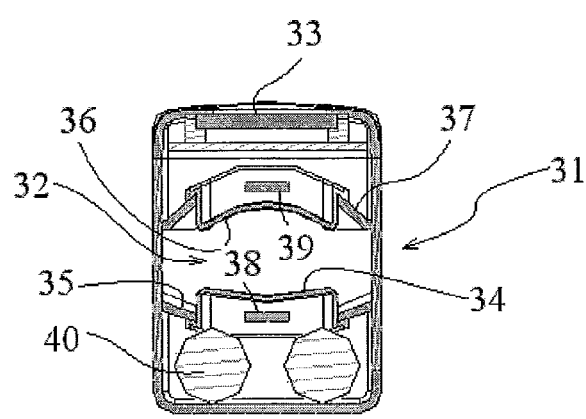
FIG. 3C is a transverse section view along a line B-B in FIG. 3A.

According to a third embodiment of the present invention, as shown in FIGS. 3A, 3B and 3C, a soft gum fingerstall oximeter is a box like soft gum finger plate oximeter. A housing 31 in which horizontal dragging slideways for soft gum slide plates 35, 37 are provided is provided in the soft gum fingerstall oximeter. An upper soft gum fingerstall 36 and a lower soft gum fingerstall 34 are fixed to the soft gum slide plates 37, 35 respectively, while the soft gum slide plates 37, 35 are mounted on the horizontal dragging slideways for the soft gum slide plates in the housing 31 respectively. Measuring elements 39, 38 are attached to the soft gum fingerstalls 36, 34 respectively.

After the soft gum slide plates 37, 35 are dragged out of the housing 31, the upper and lower soft gum fingerstalls 36, 34 can be replaced conveniently. The measuring elements 39, 38 fixed to the soft gum fingerstalls 36, 34 respectively are connected to an interface circuit board in the housing 31 via a pin socket.

A data processing circuit board, a test report display screen 33, operation keys, a battery 40, a speaker, a mini USB data output port and the like are provided in the housing 31.

When a finger is inserted into the soft gum fingerstalls 36, 34 from an opening 32, the soft gum fingerstalls 36, 34 wrap around the finger closely with variations of the profile of the finger and cause a clamping force distributed on the clamped portion of the finger uniformly.

The soft gum fingerstalls 36, 34 have a wider elastic range, which is adaptable to a larger variation of the sizes of fingers.

The soft gum fingerstalls 36, 34 are completely provided in the housing 31 which is in a totally enclosed form, which prevents the side strong light from disturbing the measurement.

Since a pivot structure is eliminated, the reliability of the oximeter is improved.

Though the three embodiments of the present invention have been described above, those skilled in the art can understand that various modifications, improvements and substitutions can be made to the present invention, but all of these modifications, improvements and substitutions fall within the scope of the invention defined by the appended claims.

What is claimed is:

1. A soft gum fingerstall oximeter without pivot structure, wherein
the soft gum fingerstall oximeter comprises electronic elements which include a data processing circuit board, a measuring circuit board, a test report display screen, operation keys, and a battery, the measuring circuit board includes an emission circuit board and a reception circuit board which are provided opposite to each other, and the soft gum fingerstall oximeter further comprises a soft silica gel sheath in which all of the electronic elements are provided, said soft silica gel sheath has an opening through which fingers can be inserted into and form a soft gum fingerstall, and the soft gum fingerstall wraps around a finger closely with variations of the profile of the finger and causes a clamping force distributed on the clamped portion of the finger uniformly.

2. The soft gum fingerstall oximeter without pivot structure according to claim 1, wherein, the emission circuit board is provided inside the soft silica gel sheath on a side in which a measured finger contacts with an inner surface of the soft silica gel sheath in a measurement, and the reception circuit board which is provided opposite to the emission circuit board is provided inside the soft silica gel sheath on a side in which the data processing circuit board is located.

3. The soft gum fingerstall oximeter without pivot structure according to claim 2, wherein, a stainless steel connecting plate which is used to fix and protect all of the electronic elements is imbedded in the soft silica gel sheath, the stainless steel connecting plate is hot pressed to and inserted into the soft silica gel sheath to form a single unit, and the outline of the stainless steel connecting plate varies with profiles of a top surface and side surfaces of the soft silica gel sheath.

4. The soft gum fingerstall oximeter without pivot structure according to claim 1, wherein, a stainless steel connecting plate which is used to fix and protect all of the electronic elements is imbedded in the soft silica gel sheath, the stainless steel connecting plate is hot pressed to and inserted into the soft silica gel sheath to form a single unit, and the outline of the stainless steel connecting plate varies with profiles of a top surface and side surfaces of the soft silica gel sheath.

* * * * *

UNITED STATES PATENT AND TRADEMARK OFFICE
CERTIFICATE OF CORRECTION

PATENT NO.       : 8,489,166 B2
APPLICATION NO.  : 12/670281
DATED            : July 16, 2013
INVENTOR(S)      : Weihu Wang Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this
Eighth Day of September, 2015

Michelle K. Lee
*Director of the United States Patent and Trademark Office*